US007166081B2

(12) United States Patent
McKinley

(10) Patent No.: US 7,166,081 B2
(45) Date of Patent: Jan. 23, 2007

(54) METHOD FOR LOCATING, MEASURING, AND EVALUATING THE ENLARGEMENT OF A FORAMEN

(76) Inventor: Laurence M. McKinley, 355 E. Grand Ave., Suite 2, Escondido, CA (US) 92025

( * ) Notice: Subject to any disclaimer, the term of this patent is extended or adjusted under 35 U.S.C. 154(b) by 0 days.

(21) Appl. No.: 10/965,306

(22) Filed: Oct. 14, 2004

(65) Prior Publication Data

US 2005/0045191 A1 Mar. 3, 2005

Related U.S. Application Data

(62) Division of application No. 10/301,944, filed on Nov. 22, 2002.

(51) Int. Cl.
*A61B 5/117* (2006.01)
*A61B 5/103* (2006.01)
(52) U.S. Cl. ..................................... 600/587
(58) Field of Classification Search ............... 600/587, 600/594; 33/511, 512; 606/1, 102; 128/897, 128/898; 433/72, 224
See application file for complete search history.

(56) References Cited

U.S. PATENT DOCUMENTS

| 4,447,206 | A |   | 5/1984  | Ushiyama                    |
|-----------|---|---|---------|-----------------------------|
| 4,526,179 | A |   | 7/1985  | Salesky                     |
| 4,566,466 | A | * | 1/1986  | Ripple et al. ........ 606/102 |
| 4,754,713 | A |   | 7/1988  | Chatenay épouse Compagnone  |
| 5,017,134 | A |   | 5/1991  | Saito et al.                |
| 5,049,069 | A |   | 9/1991  | Salesky                     |
| 5,503,559 | A |   | 4/1996  | Vari                        |
| 5,833,458 | A |   | 11/1998 | Harrisson, III              |
| 5,871,445 | A |   | 2/1999  | Bucholz                     |
| 5,891,034 | A |   | 4/1999  | Bucholz                     |
| 6,004,133 | A |   | 12/1999 | Harrison, III               |
| 6,012,921 | A |   | 1/2000  | Riitano                     |
| 6,059,572 | A |   | 5/2000  | Riitano                     |
| 6,102,930 | A | * | 8/2000  | Simmons, Jr. .......... 606/194 |
| 6,146,390 | A |   | 11/2000 | Heilbrun et al.             |
| 6,217,335 | B1 |  | 4/2001  | Riitano et al.              |
| 6,248,110 | B1 |  | 6/2001  | Reiley et al.               |
| 6,331,112 | B1 |  | 12/2001 | Lee                         |
| 6,379,155 | B1 |  | 4/2002  | Riitano et al.              |
| 6,390,819 | B1 |  | 5/2002  | Riitano                     |
| 6,423,014 | B1 |  | 7/2002  | Churchill et al.            |
| 6,491,522 | B1 |  | 12/2002 | Jensen                      |
| 6,491,702 | B1 |  | 12/2002 | Heilbrun et al.             |
| 6,641,587 | B1 |  | 11/2003 | Scribner et al.             |
| 6,808,499 | B1 |  | 10/2004 | Churchill et al.            |
| 6,821,276 | B1 |  | 11/2004 | Lambrecht et al.            |

(Continued)

*Primary Examiner*—Max F. Hindenburg
*Assistant Examiner*—Brian Szmal
(74) *Attorney, Agent, or Firm*—Christie, Parker & Hale, LLP

(57) ABSTRACT

A method for locating, measuring and evaluating the enlargement of a foramen are provided. An instrument has a handle, an angled region, and a tip to be inserted into the foramen. An instrument can be pressed onto the foramen to determine its location and whether the empty space within the foramen is large enough for the maximum width of the tip to be inserted. If the tip cannot insert, the foramen can be cut to enlarge it enough for the tip to insert. A kit of several instruments or a single instrument with tips of different maximum widths are provided for determining the amount of empty space within the foramen through the course of the enlargement.

12 Claims, 5 Drawing Sheets

U.S. PATENT DOCUMENTS 6,821,946 B1  11/2004  Goldspink et al.
6,866,509 B1   3/2005  Jensen
6,899,719 B1   5/2005  Reiley et al.
2004/0102721 A1*  5/2004  McKinley .................. 600/587

* cited by examiner

METHOD FOR LOCATING, MEASURING, AND EVALUATING THE ENLARGEMENT OF A FORAMEN

CROSS-REFERENCE TO RELATED APPLICATIONS

This application is a divisional application of U.S. patent application Ser. No. 10/301,944, filed Nov. 22, 2002, the disclosure of which is incorporated herein by reference, as if fully stated here, for all purposes.

FIELD OF THE INVENTION

The present invention is directed to surgical instruments and methods, and more particularly to a system, method and apparatus for locating, measuring and/or evaluating the enlargement of a foramen.

BACKGROUND OF THE INVENTION

Spinal surgeons frequently must work with openings within the body known as "foramina." It may be difficult to visualize or to evaluate the size or diameter of these foramina, such as, for example, during surgery or if the foramen is very small. In this situation, locating, measuring, or evaluating the enlargement of the foramen can be very difficult. For example, the openings where nerves exit the side of the spine, called "neural foramina," are frequently very narrow. The neural foramen can be particularly narrow in patients with a common condition known as "spinal stenosis," where the spinal nerves are compressed by enlarged, arthritic facet joints. Inability to relieve this narrowing frequently will cause "failure" in back surgery, particularly when the surgery involves "decompression" or opening of the spinal canal and foramina to relieve the pressure on the spinal cord. In some patients, the neural foramen is so small that the surgeon must search to find it before attempting to enlarge it. When found, the surgeon resects pieces of the bone surrounding the foramen with surgical instruments, such as, for example, "Kerrison" ronguers, until he or she believes that the foramen has been adequately enlarged around the exiting nerve. This uncertainty about when the foramen is adequately enlarged frequently results in the surgeon overestimating the size of the foramen and discontinuing the enlargement prematurely. The greatest number of failures in spinal stenosis decompression surgeries occur because the surgeon has not adequately enlarged the foramen to provide adequate space for the exiting nerve.

Accordingly, a need exists for a system and method of finding and accurately evaluating the enlargement of foramina in patients undergoing surgery.

SUMMARY OF THE INVENTION

The present invention is directed to a system, method and apparatus for locating, measuring and/or evaluating the enlargement of a foramen.

One embodiment of the invention includes a foraminal instrument including a handle, an angular region, and a tip. For purposes of this disclosure, the term "handle" refers to a graspable region of the instrument. In such an embodiment, the tip can be shaped in any manner that allows its maximum width to be inserted into the open space in a foramen, for instance, between an exiting nerve and the edge of a neural foramen. In one preferred embodiment, the tip is substantially rounded or substantially spherical. In such an embodiment, the maximum width of the tip of the foraminal instrument can be any size between a size just smaller than the open space in an unenlarged foramen to a size approximately equal to the desired amount of open space in an enlarged foramen. For example, in a neural foramen, this preferable range would be approximately 0.5 mm to 8 mm.

In another embodiment, the angled region extends at an angle, preferably about 60 to 80 degrees, more preferably about 70 to 78 degrees, and most preferably about 76 degrees from the tip distally to the axis of the handle. In such an embodiment, the angled region may be substantially curved or substantially linear.

The invention is also directed to a foramen opening system including multiple instruments as described above, each having a tip with a different maximum width. In an alternative embodiment, the kit includes a single instrument with multiple tips with different maximum widths. By inserting tips with different maximum widths into the foramen through the course of the surgery, a surgeon is able to identify the current size or location of the open space in the foramen and how much additional enlargement is necessary.

The invention is also directed to a method of evaluating the enlargement of a foramen including locating a foramen in an unenlarged state, pressing an instrument with a tip of a certain maximum width into the foramen, determining whether the tip inserted into the foramen, and cutting away the edge of the foramen if the tip did not insert into the foramen. This procedure can be repeated until the tip of the instrument inserts into the foramen in an enlarged state.

Another embodiment also includes repeating this method with a second instrument with a larger maximum width than the first instrument. This allows the foramen to be enlarged in stages, to give the surgeon an idea of how large the open space in the foramen is throughout the course of the surgery, and how much more enlargement is necessary. Finally, in another embodiment, an instrument with a tip having a smaller maximum width is pressed near the foramen until it inserts into the foramen. This allows the foramen to be located before it is enlarged.

BRIEF DESCRIPTION OF THE DRAWINGS

These and other features and advantages of the present invention will be better understood by reference to the following detailed description when considered in conjunction with the accompanying drawings where.

DETAILED DESCRIPTION OF THE INVENTION

This invention relates to an apparatus, system, and method for locating, measuring and evaluating the enlargement of a foramen to ensure an optimal surgical outcome.

For purposes of this application, the term "foramen" refers to an opening or orifice in the body, more particularly in the spine, and the term "tip" is the end region of a projecting object. The term "unenlarged state" for a foramen refers to the size of the foramen opening before any enlargement occurs, and "enlarged state" for a foramen refers to the size of the foramen opening after it has been at least somewhat enlarged.

Figure 1:
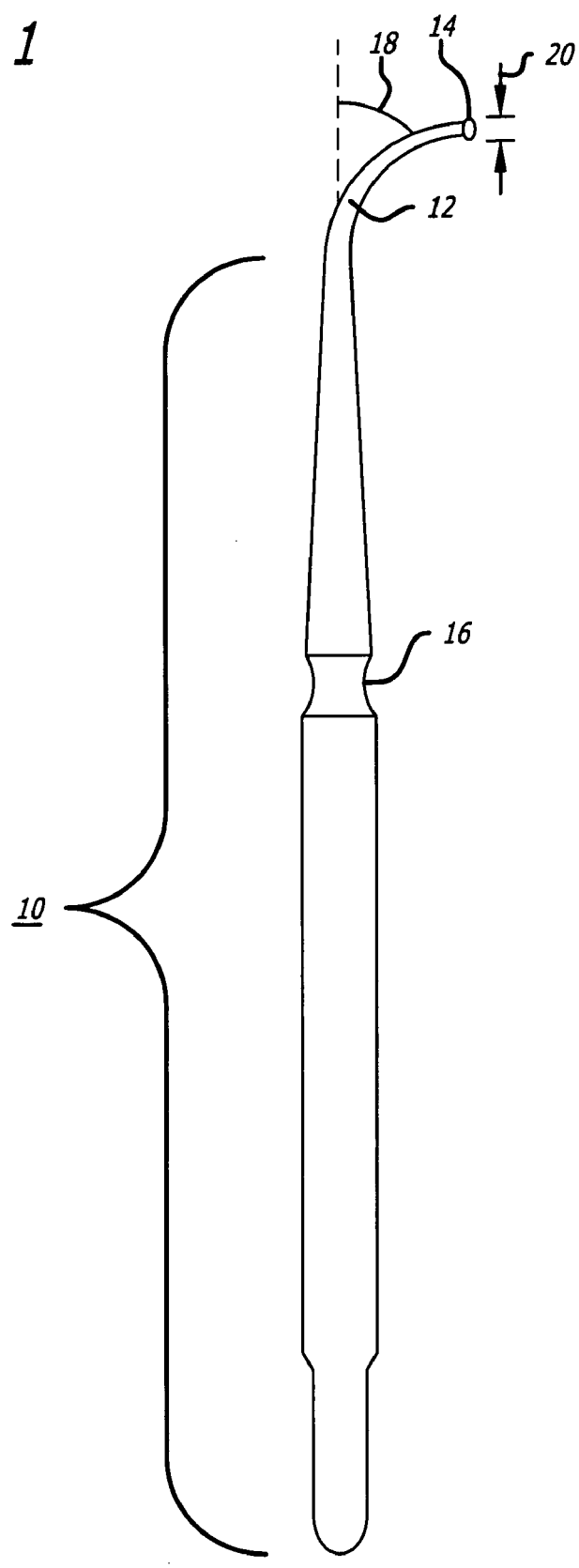
FIG. 1 shows a side perspective view of an exemplary foraminal instrument, according to one embodiment of the invention.

As shown in FIG. 1, one embodiment of the invention includes a foraminal instrument including a handle 10, an angled region 12, and a tip 14. The handle 10 is preferably around 7.5–8 cm long, but one skilled in the art will recognize that any length that can be comfortably grasped in one hand and that would extend toward the area near the foramen (not shown) would be sufficient. The handle 10 can also be textured or balanced to provide a better grasp on the instrument, and can include indentations 16 on which labels (not shown) and the like may be attached.

The angled region 12 protrudes from the handle 10 at an angle 18. In this embodiment, the angled region 12 is curved. It is also within the scope of the invention for the angled region 12 to protrude linearly at a given angle from the handle. The angled region 12 is preferably at an angle 18 of between about 60 to 80 degrees, more preferably between about 70–78 degrees, and most preferably at about 76 degrees from the tip distally to the axis of the handle 10. The thickness of the angled region 12 near the tip 14 in the embodiment shown in FIG. 1 is narrower than the maximum width 20 of the tip 14, to allow at least part of the angled region 12 to insert into the foramen (not shown) with the tip 14. However, in other embodiments, the angled region 12 does not partially insert into the foramen (not shown) and can be of any thickness as long as the maximum width 20 of the tip 14 is narrow enough to insert into the desired open space in the foramen.

Although the tip 14 in the embodiment of the invention shown in FIG. 1 is substantially spherical, it is within the scope of the invention for the tip to be shaped in any way that would allow it to be inserted into the open space of a foramen, such as the space in a neural foramen not taken up by the exiting nerve. For example, the tip may also be rounded, which allows the same approximate size of the empty space in the foramen to be determined regardless of slight changes in the orientation of the tip. However, it is also within the scope of the invention for the tip to be in any other shape the surgeon desires.

Figure 2:
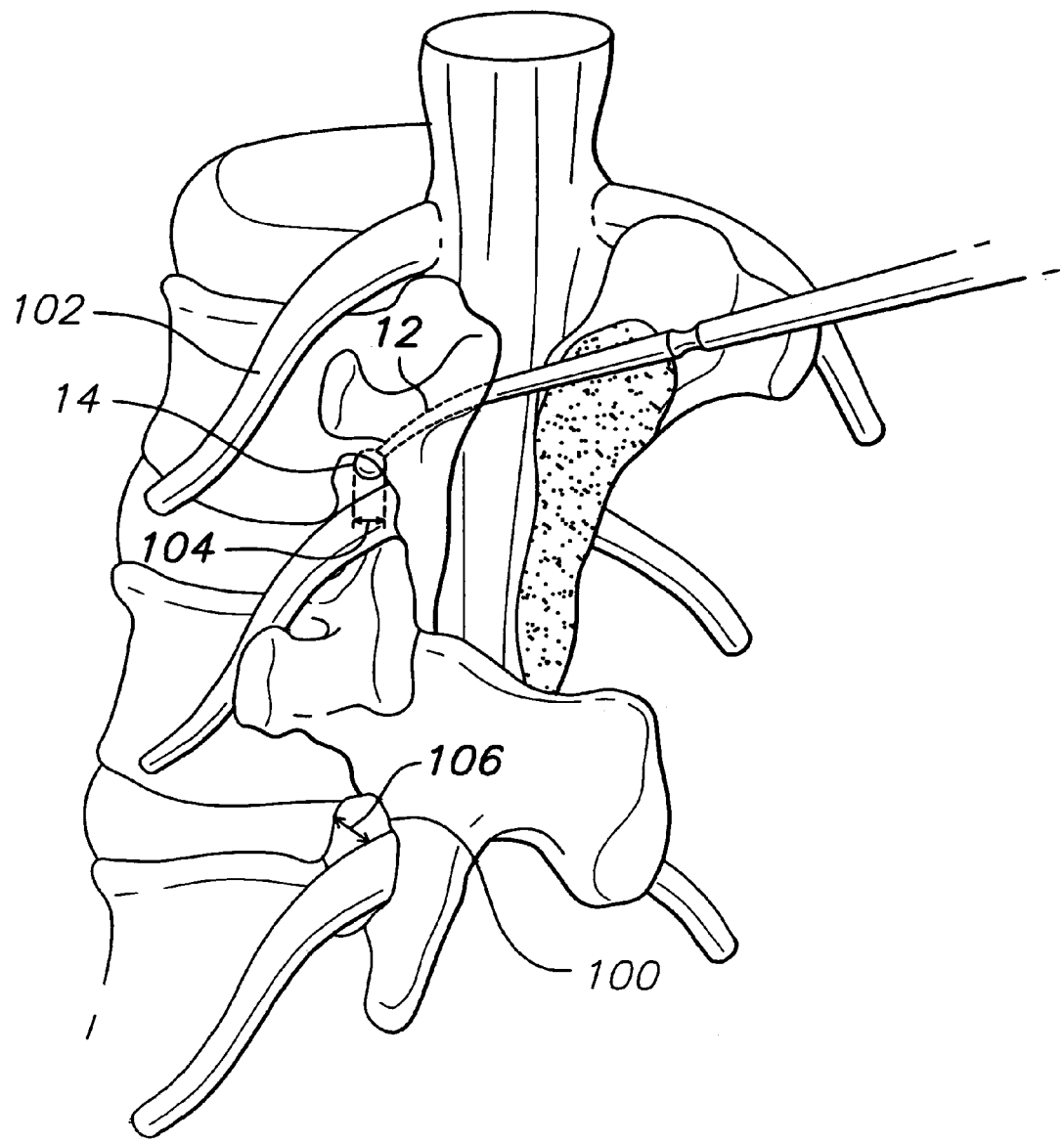
FIG. 2 shows a enlarged plan view of the tip shown in the embodiment of FIG. 1 as it is inserted into the neural foramen.

FIG. 2 shows the angled region 12 of the instrument and the tip 14 from the embodiment shown in FIG. 1 in more detail. The tip 14 is shown inserted into a neural foramen 100 in the space 106 between an exiting nerve 102 and the edge of the foramen 100. Maximum widths 104 of the tip in some preferred embodiments include: a width equal to the desired enlarged space [enlarging width] (preferably around 5 to 8 mm, and more preferably around 6 mm for a neural foramen); a width small enough to insert in the space 106 before any enlargement is made [inserting width] (preferably 0.5 mm to 2 mm, and more preferably around 1.2 mm for a neural foramen); and any intermediate width in between the enlargement and insertion widths to determine an intermediate size of the open space 106 and the extent of additional enlargement necessary.

Figure 3:
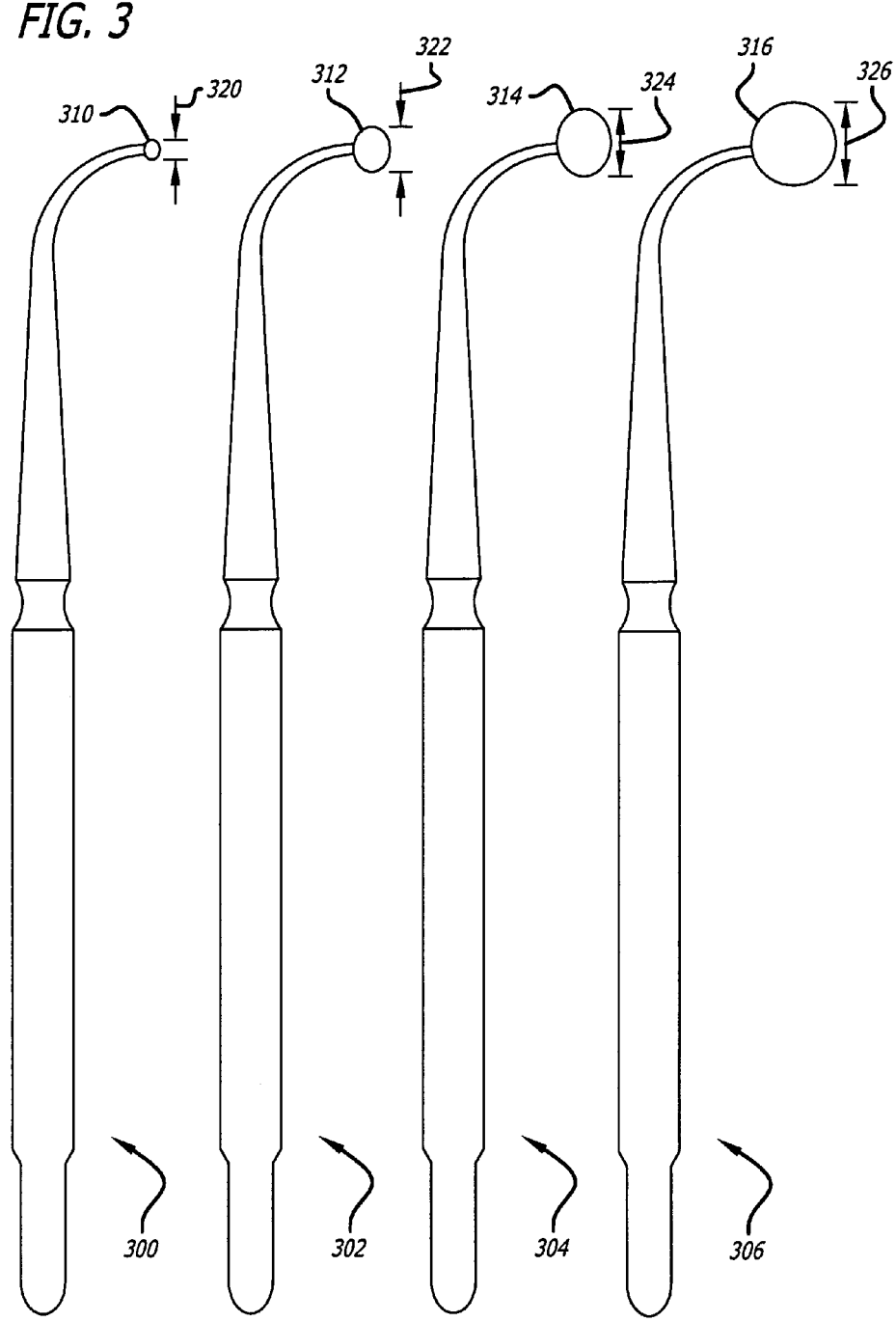
FIG. 3 shows a side view of another embodiment of a system according to one embodiment of the invention.

The invention is also directed to a foramen opening system, shown in FIG. 3. In such a system, four instruments 300, 302, 304, 306 with tips 310, 312, 314, 316 having different maximum widths 320, 322, 324, 326 are included in a surgical kit. The first instrument 300 has a maximum width 320 small enough to be inserted into a narrowed neural foramen (not shown) before it is enlarged by the surgeon. The maximum width 320 of this tip 310 is preferably around 0.5 mm to 2 mm, and more preferably around 1.2 mm for a neural foraminal instrument. The second instrument's tip 312 and the third instrument's tip 314 have intermediate maximum widths 322, 324 to provide a measure of the extent of foraminal opening. For neural foraminal instruments, the preferred maximum widths 322, 324 would be around 2 mm to 4 mm (more preferably 3 mm), and 4 mm to 5 mm (more preferably around 4.5 mm), respectively. The fourth instrument's tip 316 has a maximum width 326 equal to the desired space between the exiting nerve and the edge of the foramen (shown in FIG. 2), preferably around 5 mm to 8 mm, more preferably 6 mm for a neural foraminal instrument. Although four instruments 300, 302, 304, 306 are shown in FIG. 3, a higher or lower number of instruments can be included in the kit to locate and measure the foramen (shown in FIG. 2), depending on the needs of the surgeon.

Another embodiment (not shown) of a foramen opening system includes a single handle and an angled region, such as are shown in the embodiment of FIG. 1. However, the embodiment also includes several interchangeable tips (not shown). Each tip can be removably coupled to the angled region and has one of a selection of maximum widths, as described according to the embodiment shown in FIG. 4. The tips can be coupled to the angled region by any means capable of holding the tip in a fixed position, such as, for example, an angled region with outer threads and a tip with inner threads, etc.

Figure 5:
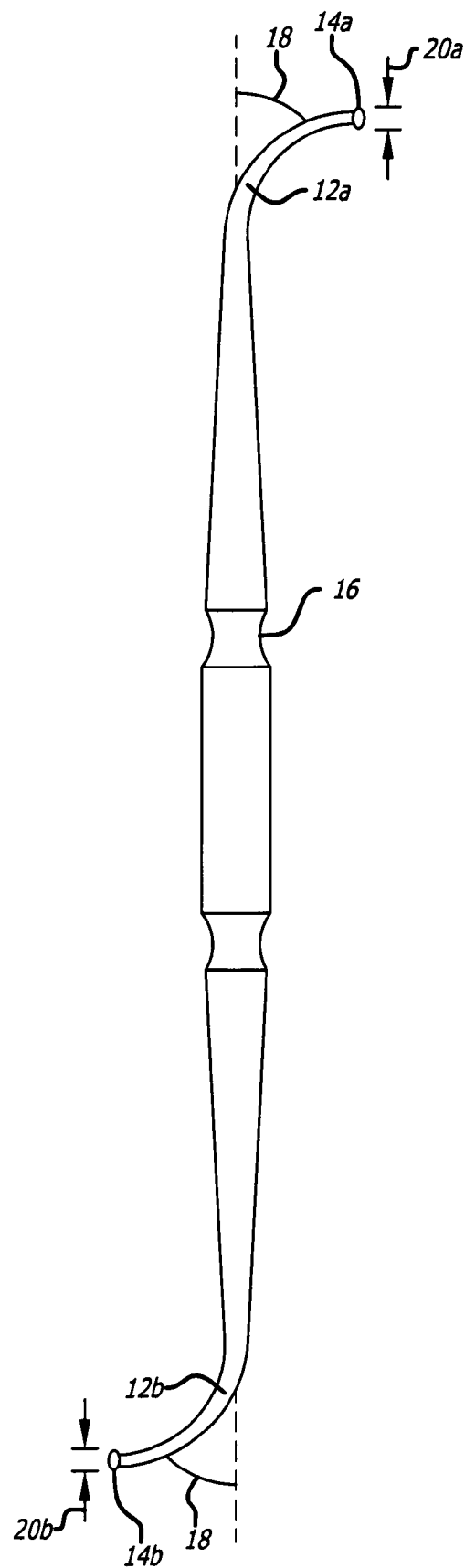
FIG. 5 shows a side perspective view of an exemplary two-tipped foraminal instrument, according to another embodiment of the invention.

Yet another embodiment of the instrument 10' shown in FIG. 5, includes two angled regions 12a and 12b fixedly coupled to each end of a handle 16. Each angled region is fixedly coupled to a tip 14a and 14b having a different maximum width 20a and 20b. This embodiment would allow a surgeon to determine the location and/or size of the foramen at two different stages of the enlargement with the same instrument.

Figure 4:
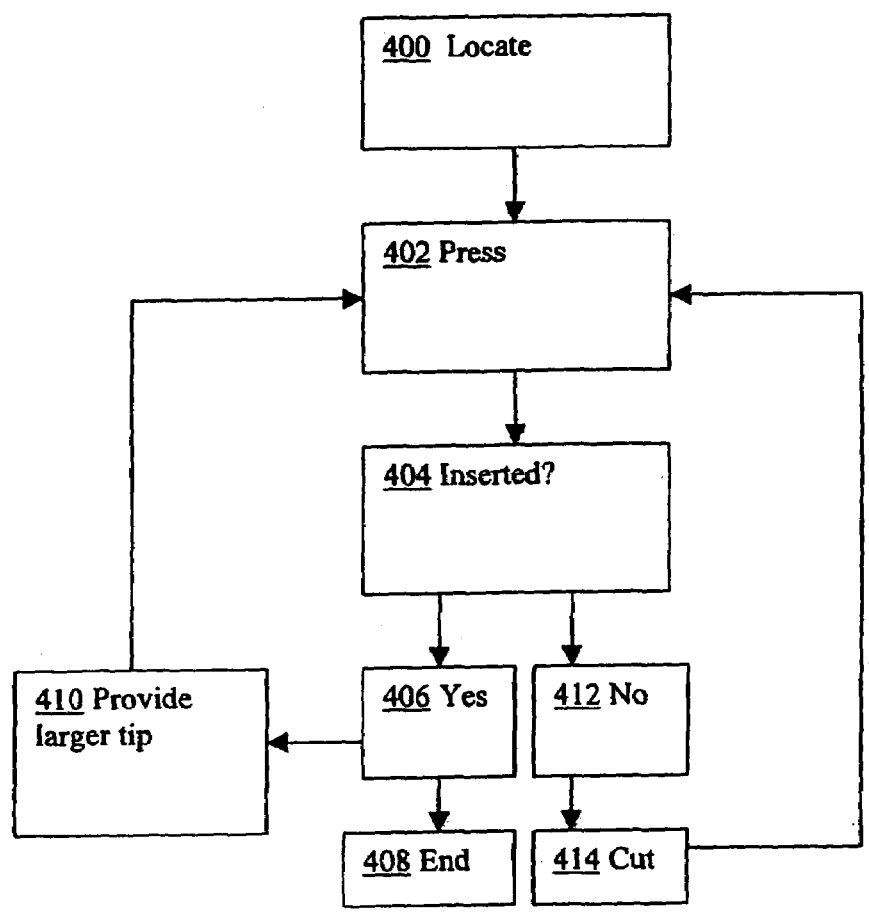
FIG. 4 is a flow chart of another embodiment of a method according to the invention.

The invention further includes a method of evaluating the enlargement of the neural foramen. Referring to FIG. 4, the method includes locating the foramen 400, pressing an instrument against the foramen 402, determining if the instrument inserts into the foramen 404, and cutting the edge of the foramen 414 if the instrument does not insert 412. The pressing 402, determining 404, and cutting 414 steps can then be repeated until the instrument inserts into the foramen 406.

In one embodiment, the instrument that is inserted into the foramen has a tip with a maximum width equal to the desired space between the exiting nerve and the edge of the foramen. Thus, the surgeon can be assured that the foramen is sufficiently enlarged when it is possible to insert this maximum width into the space and can therefore end the surgery 408.

In another embodiment, the surgeon repeats 410 this process with multiple instruments with tips of increasing maximum width in order to determine the current size of the open space in the foramen during the course of enlargement. This method can also be used with one instrument and multiple fixed or replaceable tips as discussed above. In another embodiment (not shown), the step of locating 400 the foramen includes dragging the tip of a foramen locating instrument toward the spine in the area near the foramen. The tip of the instrument preferably has a maximum width of around 0.5 mm to 2 mm, more preferably around 1.2 mm to ensure insertion into the foramen. When the tip inserts into the foramen, the surgeon is able to determine its location. The surgeon can then begin enlarging the foramen by cutting 414 the foramen's edges.

Although specific embodiments are disclosed herein, it is expected that persons skilled in the art can and will design alternate instruments and methods that are within the scope of the following claims either literally or under the Doctrine of Equivalents.

What is claimed is:

1. A method for evaluating adequate enlargement of a neural foramen comprising the steps of:
   providing a first measurement instrument, having a handle, a rigid tip with a first size defined by the maximum width of the tip, and a first rigid angled region between said handle and said rigid tip;
   locating said foramen by manipulating the first measurement instrument within the region of the neural foramen;
   measuring said foramen by pressing the rigid tip of the first measurement instrument against said neural foramen to determine the size of said foramen based on whether the maximum width of the rigid tip of the first measurement instrument can be inserted into or through the neural foramen;
   cutting away at a periphery of said neural foramen if the maximum width of the tip of the first measurement instrument cannot be inserted into said neural foramen; and
   repeating said locating, measuring, and cutting steps until the maximum width of the tip of said first measurement instrument can be inserted into or through the neural foramen.

2. The method of claim 1, further comprising the steps of:
   providing a second measurement instrument, having a handle, a rigid tip with a second size defined by the maximum width of the tip that is larger than the first size, and a first rigid angled region between said handle and said rigid tip;
   pressing the tip of the second measurement instrument against said foramen;
   determining whether the maximum width of the tip of the second measurement instrument can be inserted into the foramen; and
   cutting away at the periphery of said foramen if the maximum width of the tip of the second measurement instrument cannot be inserted into said foramen; and
   repeating said pressing, determining, and cutting steps with the second measurement instrument until the maximum width of the tip of said second measurement instrument can be inserted into or through the neural foramen.

3. The method of claim 1, wherein the step of locating further comprises the steps of:
   providing a locating instrument, having a handle and a rigid tip with a maximum width less than an open space in said neural foramen;
   pressing the locating instrument near said foramen until the locating instrument inserts into said neural foramen;
   determining a location where the tip of the locating instrument inserts into said neural foramen; and
   using said location to direct the first measurement instrument to the neural foramen.

4. The method of claim 1, wherein the rigid tip is substantially rounded.

5. The method of claim 1, wherein the rigid tip is substantially spherical.

6. The method of claim 1, wherein the first angled region forms an approximately 60 degree to 80 degree angle from the rigid tip distally to the axis of the handle.

7. The method of claim 1, wherein the first angled region forms an approximately 70 degree to 78 degree angle from the tip distally to the axis of the handle.

8. The method of claim 1, wherein the first angled region forms an approximately 76 degree angle from the tip to the axis of the handle.

9. The method of claim 1, wherein the first angled region is curved and has a diameter less than the width of the rigid tip.

10. The method of claim 1, wherein the maximum width of the tip is in the range of approximately 0.5 mm to 8 mm.

11. The method of claim 1, further comprising at least one substantially rigid substitute tip, wherein the tip and the substitute tip are removably coupleable to the angled region.

12. The instrument of claim 1, further comprising a second substantially rigid angled region having a second substantially rigid tip, said second angled region being coupled to the handle opposite the first angled region, wherein the second tip and the second angled region are sized such that the second tip is insertable into said neural foramen when said neural foramen is in at least one of an unenlarged and an enlarged state.

* * * * *